United States Patent
Shaughnessy et al.

(10) Patent No.: US 9,826,689 B2
(45) Date of Patent: Nov. 28, 2017

(54) SYSTEM AND METHOD FOR MANUFACTURING A BOTANICAL EXTRACT

(71) Applicant: TARTAN EQUIPMENT CORP., Portland, OR (US)

(72) Inventors: Timothy Lee Shaughnessy, Portland, OR (US); Ian Van Veen Shaughnessy, Portland, OR (US)

(73) Assignee: TARTAN EQUIPMENT CORP., Portland, OR (US)

( * ) Notice: Subject to any disclaimer, the term of this patent is extended or adjusted under 35 U.S.C. 154(b) by 226 days.

(21) Appl. No.: 14/733,772

(22) Filed: Jun. 8, 2015

(65) Prior Publication Data

US 2016/0353671 A1 Dec. 8, 2016

(51) Int. Cl.
*F21V 9/00* (2015.01)
*A01G 7/04* (2006.01)
*A61K 36/185* (2006.01)
*H05B 33/00* (2006.01)

(52) U.S. Cl.
CPC ............ *A01G 7/045* (2013.01); *A61K 36/185* (2013.01); *H05B 33/00* (2013.01); *A61K 2236/11* (2013.01); *A61K 2236/37* (2013.01); *Y02P 60/146* (2015.11)

(58) Field of Classification Search
CPC .................................. F21V 9/00; B60Q 1/26
USPC .................................................. 362/230, 227
See application file for complete search history.

(56) References Cited

U.S. PATENT DOCUMENTS

| | | | |
|---|---|---|---|
| 2006/0006820 A1 | 1/2006 | Roseman et al. | |
| 2012/0170264 A1 | 7/2012 | McKenzie et al. | |
| 2012/0311744 A1* | 12/2012 | Sirkowski | G01N 21/64 800/298 |
| 2014/0250778 A1* | 9/2014 | Suntych | A01G 7/045 47/1.4 |
| 2014/0287068 A1* | 9/2014 | Lewis | A01H 1/04 424/725 |
| 2016/0100529 A1* | 4/2016 | Grajcar | A01G 7/045 47/17 |
| 2016/0198640 A1* | 7/2016 | Singh | A01G 7/045 362/96 |
| 2016/0235014 A1* | 8/2016 | Donham | A01G 7/045 |
| 2016/0262313 A1* | 9/2016 | Szeto | A01G 7/045 |
| 2016/0338169 A1* | 11/2016 | Rantala | H05B 33/0857 |
| 2016/0338276 A1* | 11/2016 | Speidell | A01G 31/06 |
| 2016/0356465 A1* | 12/2016 | Polete | H05B 37/029 |

* cited by examiner

*Primary Examiner* — Edwyn Labaze
(74) *Attorney, Agent, or Firm* — Lane Powell, PC (57) ABSTRACT

A system and method for creating a botanical extract. The system comprising a grow light optimized to stimulate growth of the selected plant and an extractor using supercritical $CO_2$ to obtain the extract.

21 Claims, 5 Drawing Sheets

SYSTEM AND METHOD FOR MANUFACTURING A BOTANICAL EXTRACT

BACKGROUND

Grow lights started a horticultural revolution. The goal was to create artificial sunlight so that plants could be grown indoors and with increased growing cycles. The ability to control the light exposure allowed growers to stimulate and regulate plant growth.

Traditional grow lights are often metal halides, sodium vapor and/or arc lights. These types of light emit intense white light to closely replicate the broad spectrum of light that comprises natural sunlight, including light in the ultraviolet spectrum. Traditional grow lights had many drawbacks though. They consumed large amounts of electricity, required high capital investment in the fixtures, generated large amounts of heat and were often difficult to move and place due to their size and bulk. These factors meant that grow lights were often used for limited portions of the growing cycle or for high value cultivars where the cost was justified by the returns.

The broad spectrum light emitted from traditional grow lights is inefficient as the plant uses a small portion of the spectrum for photosynthetic activity. Each plant has a specific absorption spectrum. That is, the plant has a specific spectrum or spectra of light that it uses to perform its photosynthetic activity. Light that is outside of the absorption spectrum is not utilized. By exposing a plant to broad spectrum light, like that from traditional grow lights, the overall system is inefficient at stimulating or promoting the growth of the plant.

Operating costs for traditional grow lights are commensurately high due to the high electrical demand by the lights. The traditional grow lights use a resistive element or a spark to generate the emitted light. Both these methods of light generation require large amounts of electricity to generate the light at the necessary intensity levels.

The constant cycling and extended run time of the grow lights also causes the bulbs of traditional grow lights to fail or become ineffective in a shortened life span. The short life span means that bulbs must be replaced often, further increasing the operating costs of the lights.

If a plant has multiple absorption spectra, multiple grow lights are required to generate the corresponding light. This often requires multiple grow lights compressed into a shared space, which can be difficult to efficiently accomplish due to the large nature of many traditional grow lights.

Grow lights can be used to stimulate and promote growth of any plant. In some cases, the light is used to promote growth of Cannabis plants indoors. Due to the high value of the crop, Cannabis plants are traditionally cultivated indoors for privacy and to protect the plants from the outdoor environment. This isolation necessitates the use of grow lights to promote growth of the Cannabis plant.

Cannabis plants create Cannabinoids, the psychoactive compounds that cause the feelings of euphoria and relaxation in consumers. The Cannabinoids are produced by the plant and are found in the highest concentrations within the plant's resin. The resin is concentrated in the flowering buds of the female Cannabis plant, often appearing as sticky, dew-like droplets. The concentration of psychoactive compounds within the Cannabis resin can be increased by breeding and cultivation of the plant. New methods of Cannabis cultivation are being explored to more efficiently grow the plant and increase the concentrations of Cannabinoids within.

One of the new avenues being explored for Cannabis use is the creation of Cannabinoid rich extracts. The extracts are seen, not only as a new avenue for medical and pharmacological research, but as a more efficient and safer approach to the psychoactive use of the plant. The Cannabinoid-rich extract has a longer life and is a more stable form of Cannabinoids that can be used in many commercial and research purposes and products.

One of the most widely adopted methods of creating a Cannabinoid-rich extract from the Cannabis plant material is the use of butane as a solvent. Butane is a relatively efficient and cost effective means of extracting the Cannabinoids. However, butane is highly volatile and potentially unsafe in a gaseous form. In order to separate the Cannabinoids from the butane solvent, the butane is vaporized, causing potential safety hazards for not only the producer but also the surrounding environs and inhabitants.

Typical extraction methods use the Cannabinoid-rich Cannabis buds and surrounding leaves. The rest of the plant, stems and other leaves, are unused as it is not economical to invest resources into extracting the little concentration of Cannabinoids within the plant tissues of these parts.

There exists a need in the horticulture industry and particularly in the Cannabis cultivation industry, for improved systems and methods for plant cultivation that increase the efficiency and improve the overall safety of the growing process and products.

SUMMARY OF THE INVENTION

In accordance with the invention, novel grow lights, novel systems for refining a botanical extract and novel methods of manufacturing a botanical extract are disclosed in the accompanying detailed description.

Example grow lights have first LEDs that are coated and emit a first wavelength of light directed at a plant. The first LEDs having a first maximum operating power and a first switch controlling a power at which the first LEDs operate. A plurality of second LEDs emits a second wavelength of light also directed towards the plant. The second LEDs having a second maximum operating power and a second switch controlling the power at which the second LEDs operate. Both the first and second LEDs and the coating on the first LEDs are selected based on the absorption spectra of the plant. The first and second LEDs operated at power values less than the first and second maximum operating power, respectively.

Example systems for refining a botanical extract have an LED grow light. The LED grow light has first LEDs having a coating, the coated first LEDs emitting a first wavelength of light directed towards a Cannabis plant. The LED grow light also has second LEDs that emit a second wavelength of light towards the Cannabis plant. The first and second LEDs are selected based on the absorption spectrum of the Cannabis plant in a first and second growth phase, respectively. A first switch controlling the first LEDs and a second switch controlling the second LEDs. The first LEDs operated at a power value less than a first maximum operating power and the second LEDs operated at a power value less than a second maximum operating power. Once the first and second growth phases are completed, the plant material undergoes processing using supercritical carbon dioxide to extract a botanical extract from the processed plant material.

The botanical extraction method involves promoting a first and second growth phase of a Cannabis plant using first and second LEDs, respectively. Exposing the Cannabis plant to the first LEDs, the first LEDs emitting a first wavelength of light and having a first coating. The first wavelength and first coating selected based on the absorption spectrum of the Cannabis plant in the first growth phase. The first LEDs having a first maximum operating power and operated at a power value less than the first maximum operating power. Exposing the Cannabis plant to the second LEDs, the second LEDs emitting a second wavelength of light. The second wavelength of light selected based on the absorption spectrum of the Cannabis plant in the second growth phase. The second LEDs having a second maximum operating power and operated at a power value less than the second maximum operating power. After the first and second growth phases are completed, the whole plant is harvested. The harvested plant material is processed using a supercritical carbon dioxide extraction process to extract a botanical extract.

DETAILED DESCRIPTION

The disclosed inventions are directed to grow lights, systems for refining a botanical extract and methods of manufacturing a botanical extract. It will be understood that the invention can be applied to any plant. In the disclosure, specific reference to the Cannabis genus is made but should not be construed as a limitation of the invention.

The disclosed grow light includes multiple types of LEDs. Each type of LED emits a specific wavelength of light based on the energy band gap of the semiconductor. By varying the composition of the semiconductor material the energy band gap can be adjusted, thus varying the wavelength of the light emitted from the diode. This allows specific types of LEDs to be selected based on the wavelength of light the LED type emits. Further, the application of a coating to the LEDs can alter the wavelength of the light emitted from the LEDs. Through the selection of LEDs and coatings, a grow light can be constructed that emits light at various spectrums to improve specific plant growth performance.

The system for refining a biological extract includes first and second LEDs that are selected based on the absorption spectra of a plant during various growth phases. The first LEDs have a coating that alters the wavelength of light emitted to better correspond with an absorption spectrum of the plant. After the final growth phase, the plant is processed to extract a botanical extract. A supercritical carbon dioxide process is used to strip the extract from the plant material.

The method of manufacturing a biological extract includes promoting growth during various growth phases of the plant. Various LEDs, corresponding to absorption spectrums associated with growth phases, are used to promote the growth during specific growth phases. After the growth phases are completed, the plant is harvested. The plant material is processed, using a supercritical carbon dioxide process, to manufacture the botanical extract.

The various aspects of this invention efficiently grow a plant and further create an extract from the grown plant.

Botanical Extract System

Figure 1:
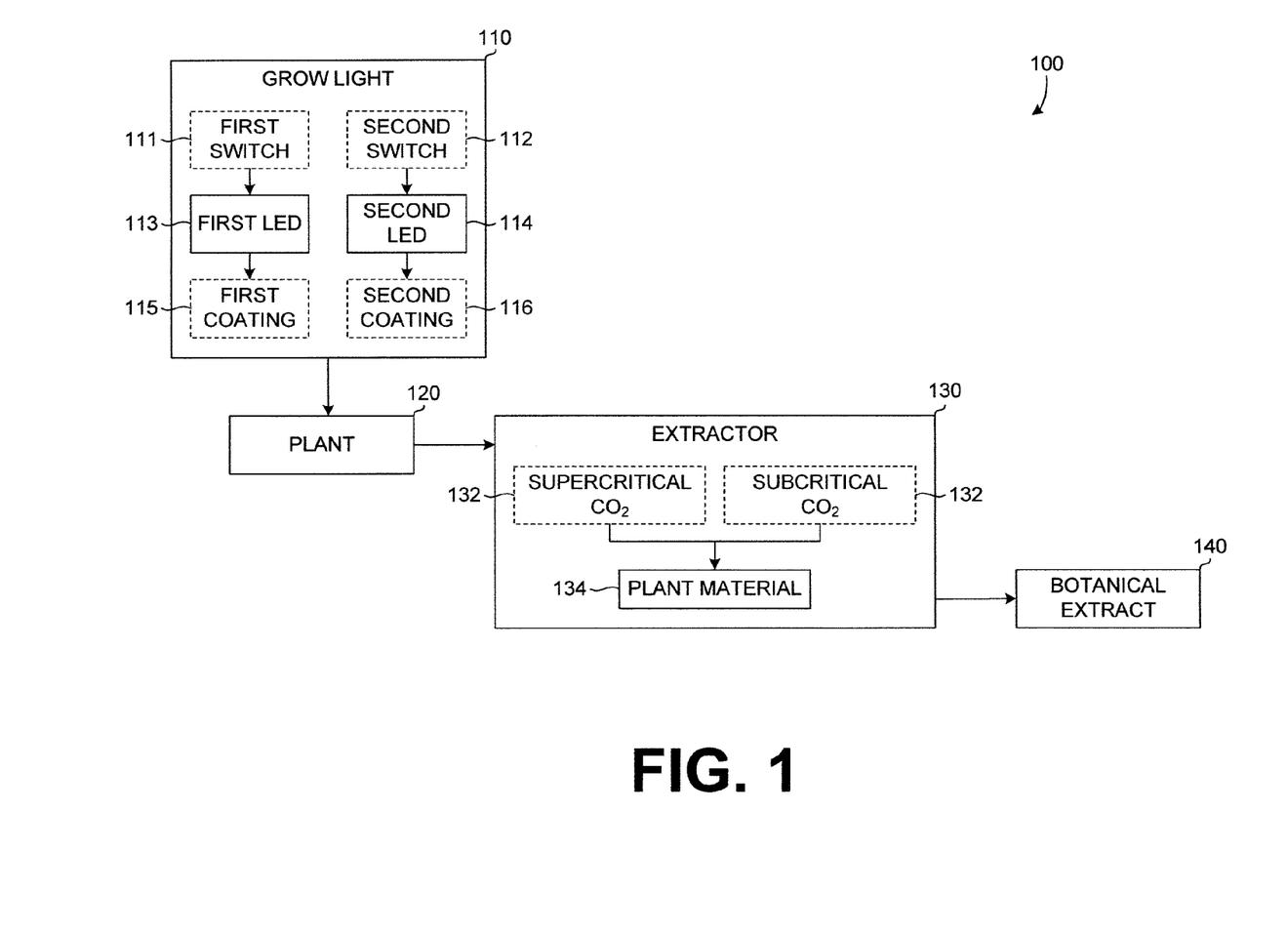
FIG. 1 is a block diagram of an example extraction system.

FIG. 1 illustrates an example embodiment of the extraction system 100. The system 100 has a grow light 110, the plant 120, and the extractor 130, which refine the extract 140.

The plant 120, as shown in the system of FIG. 1, is the component around which the rest of the system 100 is optimized. The system 100 is designed to efficiently grow the plant 120 and then process the plant material 134 to refine an extract 140. Such efficiency factors can include the time and cost to grow the plant 120, the operating costs of the system 100 and various other factors.

As with all plants, the plant 120 obtains the energy required for life from sunlight by utilizing photosynthesis. The process of photosynthesis is dependent upon the chloroplasts within the plant 120. Chloroplasts use specific wavelengths of light to carry out their processes, these specific wavelengths make-up the absorption spectrum of the plant. The absorption spectrum of the plant 120 can shift during various growth stages or phases of the plant 120. Optimizing the grow light 110 of the system 100, the growth of the plant 120 can be stimulated or promoted.

A growth phase of the plant can be the phase when the compounds of the botanical extract 140 are produced in large quantities. Promotion of this particular growth phase can increase the yield or concentration of the refined extract 140. Typically, such a growth phase comes later in the plant 120 growth cycle.

The initial growth phase is typically directed to growing the plant. During this phase, the plant 120 is creating leaves and stems to absorb the most light possible in order to prepare for a reproduction process, such as flowering or fruiting. The initial growth phase seeks to store energy and resources to optimize the reproduction potential of the plant 120.

The first LEDs 113 promote a first or initial phase of growth of the plant 120. During a first phase, the plant 120 has a specific absorption spectrum, that is, there is a specific spectrum or wavelength of light that the plant will grow most efficiently at during this particular phase of growth. The first LEDs 113 are selected based on this absorption spectrum for a first growth phase. Since various types of LEDs emit specific wavelengths of light, the first LEDs 113 can be selected based on their emitted light, the emitted light closely corresponding with the absorption spectrum of a specific plant 120.

Additionally, a coating on the first LEDs 113 can alter the wavelength or spectrum of light emitted by the LEDs. By careful selection of the first LEDs 113 based on an emitted wavelength and the application of a selected first coating 115 the emitted light from the first LEDs 113 can be optimized to promote a specific growth phase of the plant 120.

The second LEDs 114 emit a second wavelength of light corresponding to a second absorption spectrum of the plant 120. Selection of the second LEDs 114 is based on this second absorption spectrum of the plant 120. The second LEDs emit light that stimulates or promotes growth of the plant 120 in a second growth phase.

As with the first LEDs 113, the second LEDs 114 can optionally have a second coating 116. The second coating 116 alters the wavelength or spectrum of light emitted from the second LEDs 114. The second coating 116 is selected to optimize the emitted wavelength of light from the second LEDs 114, such that the light irradiating the plant 120 corresponds to a second growth phase absorption spectrum.

The wavelength of light emitted by the second LEDs 114 is typically different from the wavelength of light emitted by the first LEDs 113. However, for certain plants where the absorptions spectrums are closely spaced, the first and second LEDs, 113 and 114, may be of the same type. Each of the first and second LEDs, 113 and 114, emitting the same wavelength, but each may feature different coatings, 115 and 116, that alter the wavelengths or spectra to be different and/or overlapping.

A first switch 111 is used to control and regulate the power to the first LEDs 113. The first switch 111 controls the actuation of the first LEDs 113, cycling the LEDs on and off to mimic the light cycle the plant 120 would normally experience in a natural, outdoor environment. However, the light cycle can be modified to accelerate the growing process. The first switch 111 can be set to activate the first LEDs 113 for an extended period of time to promote growth in a first phase of the plant 120.

In addition to controlling the activation of the first LEDs 113, the first switch 111 also regulates the amount of power supplied to the first LEDs 113. Regulating the power supplied to the first LEDs 113 by the switch 111 means the first LEDs 113 can be run at less than full power. Since LEDs emit light of only a certain wavelength, reducing the power supplied to the first LEDs 113 will decrease the intensity of the emitted light without significantly altering the wavelength of the emitted light. Since LEDs can be packed relatively densely within the grow light 110, the reduction in intensity can have minimal effect on the growth of the plant 120. The reduction of operating power will also decrease the amount of electricity consumed and can extend the lifespan of the LEDs. Both the extended lifespan and reduced energy consumption, lowers the operating costs for the grow light 110, improving efficiency of the overall system 100.

A second switch 112 controls and regulates the power supplied to the second LEDs 114. In a manner similar to the first switch 111, the second switch 112 controls the cycling of the second LEDs 114 and regulates the power supplied in order to operate the second LEDs 114 at a power level less than full power. Operating the second LEDs 114 at a reduced power level decreases the intensity of the emitted light, but also results in energy savings. The energy savings decrease the overall operating costs for running the second LEDs 114 and increases the overall efficiency of the system 100.

Both the first LEDs 113 and second LEDs 114 have a maximum operating power. That is, there is a power value associated with the maximum output or intensity of the first and second LEDs 113 and 114. The first LEDs 113 have a first maximum operating power and the second LEDs 114 have a second maximum operating power that may be the same or different than the first maximum operating power. The first and second switches, 111 and 112, control the amount of power to the first and second LEDs 113 and 114, respectively. By controlling the amount of power to each the first LEDs 113 and/or second LEDs 114, the power consumption of the grow light 110 can be regulated. The first and second LEDs, 113 and 114, can be operated at power values less than the maximum operating powers to conserve energy. In the example embodiment shown in FIG. 1, the first LEDs 113 are operated at a power value approximately 63% of the maximum operating power. The reduction in the operating power conserves energy, reducing running costs and increasing the overall efficiency of the system 100.

The light emitted from the grow light 110 is radiated onto the plant 120. The plant 120 is positioned below and a distance away from the grow light 100. The distance the plant 120 is spaced from the grow light 100 is related to the intensity of the light reaching the plant 120. If the plant 120 requires a higher intensity of light for optimal growth, the grow light 100 can be positioned closer. Alternatively, using the first and/or second switches, 111 and/or 112, the intensity of the light emitted from the grow light 100 can be increased.

As the plant 120 grows, the overall height of the plant begins to increase. The grow light 100 can be moved to a new position to maintain or set a new desired spacing between the plant 120 and the grow light 100. Additionally, as the plant 120 grows, the intensity requirement for the light may change. The switches 111 and 112 can be used to adjust the intensity of the emitted light to match the light requirements of the plant 120.

In the embodiment shown in FIG. 1, the plant 120 is a generic plant. As all plants require light for photosynthesis, the system 100 and grow light 110 can be optimized, with the various components selected based on the specific growing characteristics and requirements of the plant 120.

In an embodiment of the invention, the plant 120 can be selected from the Cannabis genus. Exposing Cannabis plants to specific wavelengths or spectra of light during their growth phases stimulates and promotes the growth of the plant and the Cannabinoids within. The Cannabinoids are one of the main compounds commercial Cannabis growers are trying to cultivate and extract from the plant. Careful selection of the components of the system 100 allow the system 100 to be optimized to promote growth of a Cannabis plant. The system 100 can be further refined to a particular species of a Cannabis plant or optimized to promote production of desired compounds within the plant.

Once the plant 120 has matured to a desired point, the plant 120 can be harvested. The harvested plant material 134 is placed within an extractor 130. In this example, the extractor 130 uses supercritical $CO_2$ 132 to extract compounds from the plant material 134 within the extractor 130. The supercritical $CO_2$ 132 flows over and through the plant material 134 extracting compounds and suspending them in solution with the supercritical fluid.

By controlling the pressure within the extractor 130 and the temperature of the plant material 130 and supercritical $CO_2$ 132, a user can selectively extract compounds from the plant material 134. The supercritical $CO_2$ extraction process targets compounds within the plant material 134 that have certain chemical properties. By varying the parameters of the extraction process, the user can selectively extract compounds from the plant material 134. The ability to target specified compounds using the extractor 130 increases the efficiency of the system 100 in refinement of a botanical extract 140.

In order to refine the botanical extract 140, the extracted compounds are separated from the super critical $CO_2$ 132 solvent. There are many methods of accomplishing the separation of the extracts from the solution. These methods can be conducted within or outside of the extractor 130. To conduct the process outside of the extractor 130, the extract rich solution can be transferred to a different area or machine to undergo further processing to refine and separate the supercritical $CO_2$ from the botanical extract 140.

The easiest method to accomplish the refining or separation of the botanical extract 140 is to expose the extract rich supercritical $CO_2$ 132 solution to normal temperature and pressure conditions. When exposed to these conditions, the supercritical $CO_2$ 132 boils off as $CO_2$ gas from the solution, leaving behind a refined botanical extract 132. While this method is simple, the $CO_2$ is lost to the atmosphere and new supercritical $CO_2$ is needed for further extractions.

In a preferred embodiment of the invention, the $CO_2$-extract separation is done in a vessel in order to capture the $CO_2$. The recaptured $CO_2$ can then be chilled and pressurized to once again become supercritical $CO_2$ 132 for reuse in the extractor 130. The recovery of the used $CO_2$ solvent assists in minimizing the overall running costs of the system 100 and further increases the efficiency of the system.

The use of supercritical $CO_2$ to refine the botanical extract 140 also ensures that compounds within the extract 140 are not exposed to undue heat as they might be in other extraction processes, such as hydrocarbon based extraction processes. Exposure to heat can cause the extracted compounds to undergo chemical reactions, which reduces the concentration of usable compounds within the extract 140. The supercritical $CO_2$ extraction process is a low temperature process that preserves the quality of the extracted compounds.

The extractor 130 can also perform subcritical $CO_2$ extraction processes. In the subcritical $CO_2$ process, subcritical liquid $CO_2$ 136 flows through the plant material 134. The subcritical $CO_2$ 136 acts as a solvent, extracting compounds from the plant material 134. In comparison to the supercritical $CO_2$ 132, the subcritical $CO_2$ 136 is a much reduced solvent. The subcritical $CO_2$ 136 can extract lighter compounds such as oils, but cannot extract heavier compounds such as waxes. The use of subcritical $CO_2$ 136 for the extraction process allows for the targeting of the extraction, whereby only the lighter oils are extracted as desired or selected. The lighter Cannabinoid oils do not require further refinement to remove the heavier waxes as can be necessitated by the use of supercritical $CO_2$ 132. The subcritical $CO_2$ 136 process can take more time and yield less than the supercritical $CO_2$ 132 extraction process. However, the trade-off of efficiency and time can be desired as the resulting oil extract product may not require refinement like the supercritical $CO_2$ 132 extract product might.

As with the supercritical $CO_2$ 132 extraction process, the subcritical $CO_2$ 136 can be recovered after the extraction is completed. The subcritical $CO_2$ extract solution can be processed in similar manners as the supercritical $CO_2$ extract solution. Once the refinement is complete, a resulting Cannabinoid rich extract is produced.

In the embodiment of the system 100 as shown in FIG. 1, the plant 120 is a generic plant from which a botanical extract 140 is formed. The botanical extract 140 contains compound(s) or chemicals that are extracted from the plant material 134. It will be understood that any species or type of plant can be used in the system 100.

In an embodiment of the system 100, the plant 120 can be from the Cannabis genus as mentioned above. A possible botanical extract 140 could include a Cannabinoid rich extract. The Cannabinoid rich botanical extract 140 is refined from a Cannabis plant 120. The Cannabinoid rich extract can be used in numerous pharmacological, recreational and other processes as desired.

Grow Light

Figure 2:
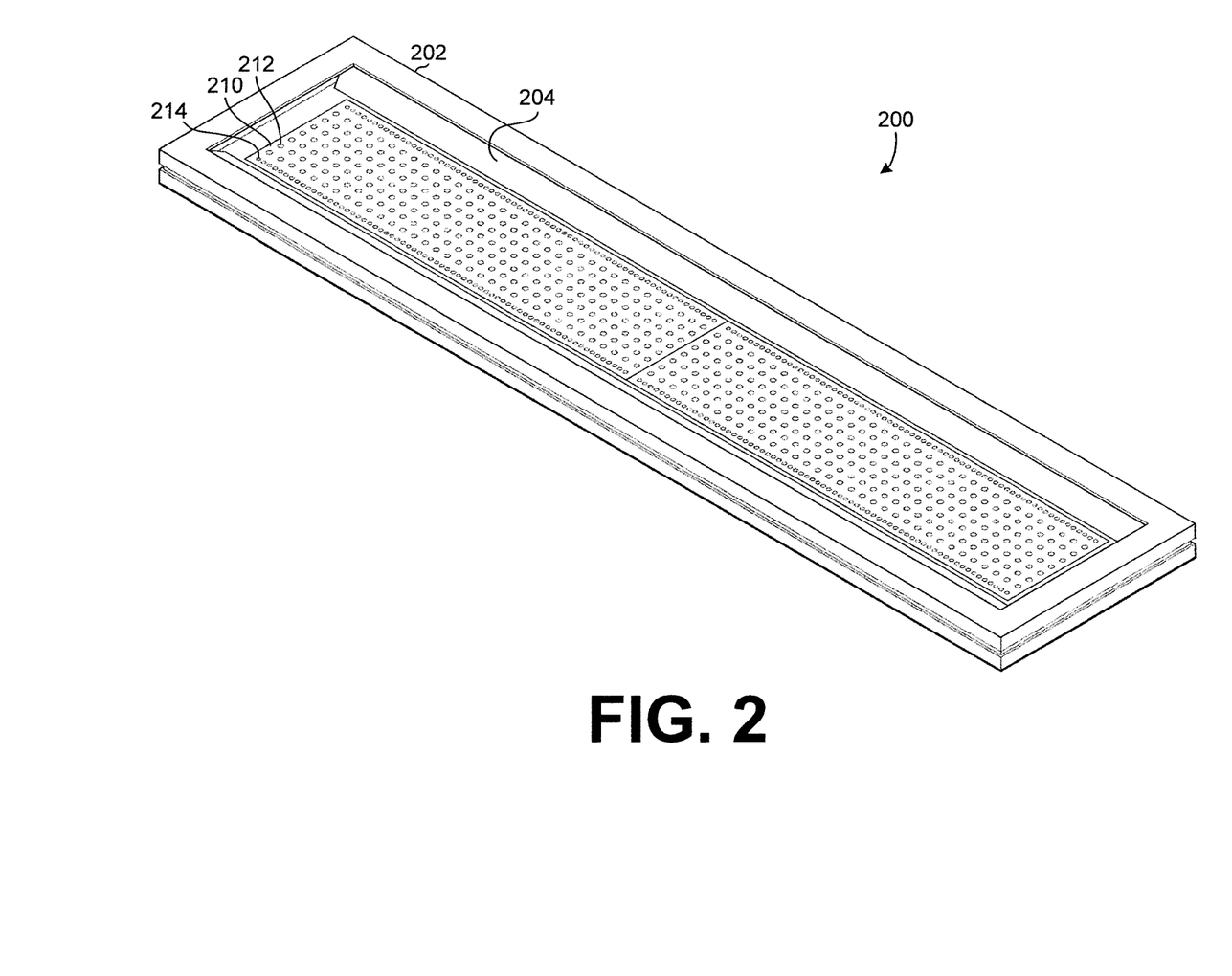
FIG. 2 shows an example grow light.

FIG. 2 is an embodiment of a grow light 200 according to the invention. The grow light 200 has a housing 202 having reflectors 204 and containing a substrate 210 to which light emitting diodes (LEDs) 212 and 214 are mounted. The grow light 200 emits light that is configured to promote the growth of a plant.

The housing 202 of the grow light 200 shown in FIG. 2 provides the overall structural frame for the grow light 200 and the mounting point for the substrate 210 containing the LEDs 212 and 214. The housing 202 can be open on a single side to emit the light, as shown in FIG. 2, or the housing can be open on both the front and back side. An open style housing can assist with the heat dissipation from the LEDs 212 and 214.

In the embodiment shown, the housing 202 is constructed to form a rectangular shape. The shape of the housing 202 can be dictated by the arrangement of the LEDs, 212 and 214, and the shape of the substrate 210. The arrangement of the LEDs 212 and 214, and the shape of the substrate 210 can be, in turn, dictated by the growing specifications or characteristics of the plant that is exposed to the grow light 200. Depending on the necessary or desired intensity and spectra of emitted light, the arrangement, spacing and quantity of the LEDs 212 and 214 can vary depending on the plant the grow light 200 is promoting growth. The housing 202 is designed and constructed to contain the optimized or desired substrate 210 shape and the arrangement of the LEDs 212 and 214.

The housing 202 as shown in the FIG. 2, is constructed of a metal, such as aluminum. The housing can be formed as a single cast piece, a single machined or formed piece, or constructed of multiple elements. In the embodiment shown, the housing 202 is formed of multiple sidepieces that are assembled and affixed together to form the singular housing 202. Multiple methods of assembling a multi-piece metallic housing are known and can include soldering, welding, adhesives, fasteners or some combination of those. In other embodiments, other metals can be used to construct the housing 202. The alternative metals can be selected based on a number of factors such as cost, strength, weight and the ease of use in the forming process.

A metallic housing has multiple benefits. It can be both lightweight, structurally rigid and can provide the necessary heat dissipation required for operating a grow light. Constructing the housing of a metal, such as aluminum, allows the use of the thermal properties of the metal material to remove the thermal energy created by operating the LEDs. The LEDs 212 and 214 are mounted on the substrate 210, with the light emitting portion on the substrate surface directed outwards. The electrical connections for the LEDs 212 and 214 are contained on the reverse side of the substrate 210, interior to the housing 202. The space between the housing 202 and the substrate 210 constrains the heat generated during operation of LED, 212 and 214. At a threshold level, the temperature generated can begin to adversely affect the LEDs, 112 and 114. The adverse effects can include those such as shortening the life span of the LEDs and/or reducing operating efficiency. By using metal to construct the housing, the high thermal conductivity of the metal material can be used to have the housing act as a heat sink for the thermal energy generated by the LEDs. Additionally, the housing 202 can be shaped or formed in order to increase the thermal sink characteristics of the housing 202 as desired. Such options can include sculpting the housing 202 to increase the surface area for improved thermal transfer or increasing the thickness of the metal in areas to increase the thermal storage capacity of the housing 202.

An additional benefit of using the grow light 200 housing 202 as a heat sink is that the thermal energy from the LEDs is transferred through the housing 202 and into the surrounding environment. The transfer of thermal energy raises the temperature of the environment surrounding the plants, which can further stimulate the photosynthetic activity within the plant, thus promoting further growth of the plant. The additional heat can also be necessary to stimulate certain growth phases of the plant.

Alternatively, the housing can also be constructed of other materials, such as plastics or composites. Alternative materials may be chosen for a number of factors, including the environment in which the grow light 200 is deployed, the housing 202 cost per grow light 200, the weight of the overall housing 202, and ease of construction and installation of the grow light 200. In an example embodiment where the housing is large, a stronger, lighter material than metal may be desired in order to maintain the rigidity of the housing over the extended, unsupported length of each side. In further embodiments, multiple materials can be used to construct the housing 202.

The housing 202 is typically attached to a support structure in order to orient the light towards a growing plant. In some situations, the grow light may be supported by a ground-mounted structure such as a poll. In most indoor growing situations the grow lights 200 are suspended from a roof or supporting structure such that the grow light 200 is suspended above the plant(s). The required attachment points for mounting or suspending the grow light 200 can be integral to the housing 202 or can be affixed to the exterior of the housing 202. The grow light embodiment shown in FIG. 2 is designed to be suspended above the growing plant(s). Suspending the grow lights can be desirable in many growing situations since the suspended lights can be raised as the plant(s) grow taller, thereby easing the labor required to reposition the grow lights 200. Additionally, suspending the grow lights 200 allows them to be aimed by raising or lowering one or more sides to direct the light as desired towards a growing plant(s).

The housing 202 can also have a reflector 204 disposed about its interior, as shown in FIG. 2. The reflector 204 reflects the light emitted by the LEDs, 212 and 214, directing the light onto the growing plant. The reflector 204 is highly reflective material, configured to reflect, diffuse, concentrate and/or direct the light. Possible materials that can be used in the reflector 204 include a polished sheet of metal, a mirror, Mylar or other such material.

The use of Mylar or other formable material as the reflector 204 material allows complex shapes or curves to be integrated into the reflector 204. A complex shaped reflector 204 may be employed in order to better reflect or distribute the light accurately or evenly as desired or required. In shaping the reflector, the reflector 204 can evenly distribute the intensity of the emitted light, thus ensuring each plant receives the requisite or desired light exposure.

Alternatively, the reflector can be a hard, rigid material, such as a metal or glass, which can then be shaped to the desired reflector 204 shape. By using a stronger, more rigid material, the reflector 204 can provide additional internal support to the housing 202, increasing the rigidity and/or strength of the housing 202.

The substrate 210 of the light 200 restrains the LEDs 212 and 214 in a desired configuration or pattern. In the embodiment shown in FIG. 1, the LEDs 212 and 214 are of the surface mount type and are disposed across the face of the substrate 210 in a predetermined pattern. The electrical connections between the LEDs 212 and 214 and a power supply (not shown) are disposed on the rear face of the substrate 210, i.e., the face interior to the housing 202. The substrate 210 can be prepared in advance to receive the LEDs, with the contact pattern disposed on the surface prior to the affixment of the LEDs 212 and 214.

The substrate 210 can be constructed of a number of materials, such as a polymer, metal, ceramic or composite. In the example shown in FIG. 2, the substrate 210 is constructed of metal. The use of metal as the substrate 210 allows the substrate 210 to act as a thermal sink for the heat generated by the LEDs 212 and 214 during operation. The substrate 210 may further be in thermal communication with the housing 202 thereby providing a path by which the generated heat can be exhausted to the surrounding environment. Additionally, the substrate 210 can strengthen the housing 202 of the grow light 200. In spanning across the housing 202, the substrate 210, when affixed to the housing 202, increases the rigidity of the housing 202.

In alternative embodiments, the substrate 210 can be constructed of a material such as ceramic. The ceramic substrate can function as a thermal sink for the generated heat; however, the ceramic substrate can be lighter than a metallic substrate having similar thermal and/or structural properties. The material used to construct the substrate 210 can be selected based on a number of design considerations, including cost, strength, thermal properties and others.

The grow light 200 as shown in FIG. 2 contains two substrates 210 having LEDs 212 and 214 disposed across their surfaces. Multiple or a singular substrates can be disposed in the housing 202 of the grow light 200. In an embodiment the substrate 210 can be similar to a tile, in which each substrate 210 tile has a standard size, shape and arrangement of LEDs. These substrate 210 tiles can then be assembled or arranged in a desired or optimized pattern to further increase the efficiency of the grow light 200 in promoting growth in a plant. The use of tile-like substrates 210 allows the grow light 200 to be easily configured for an environment and eases the burden of manufacturing as each tile is a standard item.

The LEDs 212 and 214 are disposed across the face of the substrate 210 and emit light that is directed out of the grow light 200 and towards a growing plant. The emitted light is configured to stimulate and/or promote the overall growth or specific growth characteristics of the plant. Selection of the LEDs 212 and 214 can be performed so as to target a specific plant and can further be optimized to enhance or promote a specific characteristic of the plant.

Unlike typical grow light bulbs, the heat generated during operation of LEDs, such as 212 and 214, is not generated by a filament, but rather at the electrical connections. The electrical connections for the LEDs 212 and 214 as shown in the embodiment of FIG. 2 are located on the back of the substrate 210. During operation of the LEDs 212 and 214, the heat generated is therefore generated on the back side of the substrate 210. The substrate 210 is mounted within the housing 202, with the backside of the substrate 210 spaced a distance from the interior of the housing 202. The generated heat can accumulate in the gap between the substrate 210 and housing 202. At a threshold level, the accumulated heat can adversely affect the LEDs 212 and 214.

In order to assist with heat mitigation, a number of design features and techniques can be employed within the grow light 200.

In an embodiment, the substrate 210 can act as a thermal sink, absorbing the thermal energy generated during operation of the LEDs 212 and 214. As the substrate 210 gains thermal energy, the thermal energy is dispersed throughout the substrate 210. The thermal energy can be exhausted from both sides of the substrate 210 to the surrounding environment. Additionally, the substrate 210 can be in thermal communication with the housing 202, which increases the effective surface area available for transferring thermal energy to the surrounding environment.

In another embodiment, the housing 202 is not enclosed on the back side of the substrate 210, rather the housing 202 is a frame that wraps around the periphery and supports the substrate 210. A housing 202 of this configuration exposes the back side of the substrate 210 to the surrounding environment, allowing the thermal energy to be radiated away from the substrate 210 rather than being confined by the housing 202.

Further, the substrate 210 can feature elements that increase the surface area of the substrate 210. The increased surface area of the substrate 210 increases the thermal energy dissipation to the surrounding environment. Such design features could include fin-like or other structures that are formed or placed on the substrate 210, which further increase the surface area of the substrate 210.

Alternatively, to assist with heat mitigation, a fluid can be used to assist in convecting thermal energy away from the substrate 210 and LEDs 212 and 214. Possible means for convecting the thermal energy include increasing airflow over the substrate 210 and the use of circulating fluid around or over the substrate 210 to remove thermal energy.

When LEDs 212 and 214 are densely packed, as shown in the embodiment in FIG. 2, this can lead to overheating issues. If LEDs overheat, the efficiency and lifespan of individual LEDs can be significantly lessened. In the embodiment shown, the substrate 210 is constructed from a relatively thick piece of aluminum. The aluminum substrate 210 has thermal properties such that it can act as a thermal sink for the LEDs. In this manner, the substrate 210 draws the generated heat away from the LEDs, 212 and 214, and dissipates the heat into the surrounding environment. The surrounding environment can include the housing 202 itself and the air gap between the substrate 210 and the housing 202. It may be desirable to have the substrate 210 in thermal communication with the housing 202 to increase the efficiency of heat dissipation from the grow light 200. Alternatively, the substrate 210 can be shaped or contoured to increase the surface area to better dissipate the generated heat. Other suitable materials, shapes, or combinations thereof can be used to construct the substrate 210 to aid the efficiency of heat dissipation as desired.

In the grow light 200, the first LEDs 212 generate a first level of heat and the second LEDs 214 generate a second level of heat during operation. By controlling the power level at which the first LEDs 212 and second LEDs 214 are operated, the first and second levels of heat generated can be controlled. Reducing the operating power of the first LEDs 212 and/or second LEDs 214 reduces the generated heat levels respectively. In the example shown in FIG. 2, the combined temperature output of the first and second heat levels is 120° F. or less, which is done by regulating the operating power levels of the first and second LEDs, 212 and 214.

LEDs, such as 212 and 214, emit light in a spectrum of about 30-40 nm in width. The actual emitted wavelength or spectrum of light can be varied by altering the band gap energy of the semiconductor that is the LED. The band gap energy can be altered by changing the composition and architecture of the LED semiconductor. This allows an LED to be constructed that emits a specified wavelength or narrow spectrum of tuned light. This means LEDs can be selected for application their emitted wavelength and/or spectra. In the case of horticulture this is desired as it allows the selection of an LED based on the absorption spectrum of a plant. In doing so, the photosynthetic activity of a plant can be optimized due to the specific light wavelengths and spectra the plant is exposed to.

The LEDs 212, as shown in the example embodiment of FIG. 2, are white LEDs. White light is an agglomeration of wavelengths and is typically measured in temperature, Kelvin (K), indicating the predominance of the colors that compose the white light. In the embodiment shown, the white LEDs, 212, emit white light at 6200 K. The temperature of the LEDs 212 indicates the emitted light tends to the blue portion of the visible light spectrum. On a spectral plot, the light emitted from the LEDs 212 has a peak in the blue wavelength region of 450-495 nm, with additional but less intense wavelengths emitted across other portions of the visible spectrum. In alternative embodiments, the first LEDs 212 can emit light having different physical properties than those described above. The first LEDs 212 are selected based on the optimization of their physical properties with a first absorption spectrum of a selected plant.

Figure 4A:
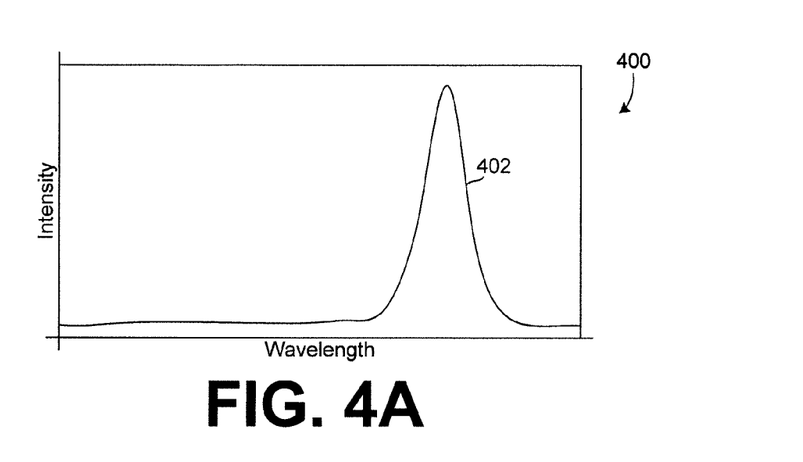
FIG. 4A is an example spectral plot of the light emitted from the first LEDs of a grow light.
Figure 4B:
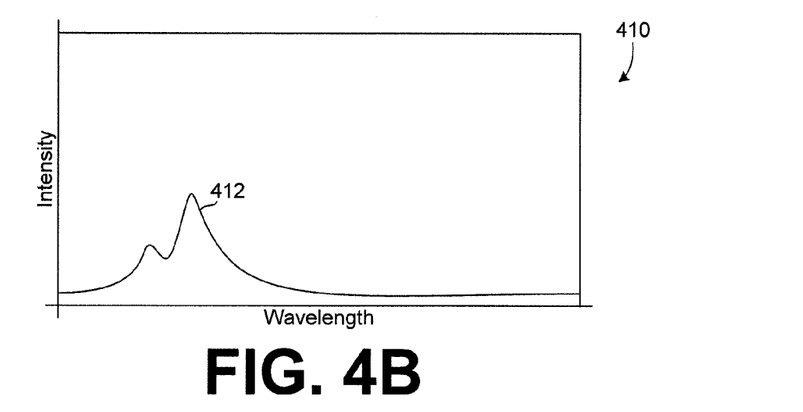
FIG. 4B is an example spectral plot of the light emitted from the second LEDs of the same grow light referenced in FIG. 4A.

FIG. 4B is an example spectral plot of the emitted light from LEDs 212, showing the relative intensities of the various wavelengths of light emitted from the LEDs 212.

The LEDs 214, as shown in the example embodiment of FIG. 2, are LEDs emitting light in the red portion of the visible light spectrum. The red portion of the visible light spectrum contains wavelengths ranging from 620-750 nm. The LEDs 214 of FIG. 2 emit light at an approximate wavelength of 660 nm. Other wavelengths are emitted, but the highest intensity is at the 660 nm wavelength. In alternative embodiments, the second LEDs 214 can emit light having different physical properties than those described above. The second LEDs 214 are selected based on the optimization of their physical properties with a second absorption spectrum of a selected plant.

An example spectral plot of the light emitted from the LEDs 214 is shown in FIG. 4A. The spectral plot shows the greatest intensity of light about the 660 nm wavelength, with a rapid tapering of intensity to either side corresponding to the surrounding wavelengths.

The LEDs, 212 and 214, are typically operated in a cyclical manner. Whereby switches and/or a control system cycle the LEDs, 212 and 214, on and off to mimic the light cycle a plant would normally experience. The cycle can be altered to extend the light cycle thereby accelerating or promoting the growth of a plant.

Further, only a portion of the LEDs, 212 and 214, can be operated at a given time. This allows for the control of the intensity of the emitted light and the amount of energy used to operate the LEDs 212 and 214. The operation of the LEDs, 212 and 214, can be optimized based on the particular growth phase or life stage of the plant at a given time. The optimization for the emitted light to a plant at a given life stage or growth phase increases the efficiency of the grow light 200. Excess grow light 200 use and energy consumption is minimized by the optimization.

In the embodiment shown in FIG. 2, the LEDs 212 are selected to promote or stimulate growth of a plant in an initial growth phase. The initial growth phase can include the formation of stems, leaves and an overall healthy and mature plant. During this phase, the operation cycling of the lights and the light intensity can be monitored and altered to optimize the growth of the plant. The optimization can be done manually or automatically based on observed plant growth status or based on sensors that monitor the characteristics or properties of the growing plant and environment.

In a second growth phase, the LEDs 214 can be operated, simultaneously or independently of the LEDs 212. That is both the LEDs 214 and 212 can be activated or only the LEDs 214 can be activated. The LEDs 214 can stimulate or promote a second growth phase of the plant. The second growth phase could include flowering, fruiting or a secondary growing phase. If the LED's 214 and 212 are simultaneously activated or operated, the LEDs may be operated a varying power levels to match optimal light exposure of the plant. Further, as with the LEDs 212 described above, the LEDs 214 can be operated to optimize the light emitted based on the growing plant.

Additional LED types emitting additional spectra or wavelengths can be included in the grow light 200. The inclusion of additional LEDs may be chosen depending on the absorption spectra of a plant and/or the desired plant characteristic to be optimized. The intensity and power consumption of the additional LEDs can be accomplished in similar manners as those described above for controlling the same in the LEDs 212 and 214.

The LEDs, 212 and 214, can also feature a coating(s) which alter the spectra of the emitted light. In the embodiment shown in FIG. 2, the LEDs 214 have a phosphor coating. The phosphor coating is a luminescent material, that is, the phosphor coating absorbs some of the emitted light energy and radiates light energy. Functioning like glow-in-the-dark material, the phosphor coating absorbs the light energy and can store and emit it over a longer duration or it can absorb and emit the light energy having an altered spectra or wavelength than what was initially absorbed.

When stimulated by the light emitted from the LEDs 214, the phosphor coating absorbs at least a portion of the incoming light energy. The phosphor material within the coating is stimulated by the incoming light and then radiates light itself. The emitted light can have altered wavelengths or spectra from the light that was initially absorbed. The wavelengths, spectra and intensities of the phosphor emitted light can be determined by the chemical composition of the phosphor coating. The phosphor coating can be semi-transparent, such that only a portion of the emitted light of the LEDs 214 is absorbed and altered by the phosphor coating.

In the embodiment shown in FIG. 2, the phosphor coating emits light spanning the visible spectrum, covering the green, yellow and red wavelengths. The spectrum of light released from the coated LEDs 214 can be chosen based on the initial LED 214 wavelength and the phosphor coating that is selected. The LEDs 214 and the coating can be selected to optimize or match to the absorption spectrum of the growing plant. The use of the phosphor coating on the LEDs 214 allows a specific wavelength of light emitted from the LEDs 214 to be diffused into a wider spectrum that is more optimized to the plant and its current growth stage.

In another embodiment, both the LEDs, 212 and 214, can feature phosphor coatings to optimize the emitted light. In alternative embodiments, only one or neither of the LEDs 212 or 214 can feature a phosphor coating. In yet another embodiment, additional LEDs can be included in the grow light 200 and the additional LEDs can have phosphor coatings as required or desired in order to promote the growth of a selected plant overall or in a specific growth stage.

In an alternative embodiment, the second coating of the second LEDs 214 can be a plastic or polymer that does not contain phosphor. The plastic or polymer coating can be structured protect the second LEDs 214 from external environmental factors such as moisture or dust. In a further embodiment, the plastic or polymer coating can have optical properties that modify or change the emitted light from the second LEDs 214. In an example coating, a polymer can have refractive properties that alter the angle of the emitted light, thereby directing the light in a desired direction.

The LEDs, 212 and 214, and phosphor coating(s) of the grow light 200 are selected to promote growth in a specific plant species or type. In the embodiment shown in FIG. 2, the plant selected for use of the grow light is a plant from the Cannabis species. The emitted light from the LEDs 212 stimulates an initial phase of growth in the Cannabis plant. During the initial phase, the plant produces numerous leaves with which to capture and use the light energy. The initial phase is focused on growing a large and healthy Cannabis plant. During the second phase, the LEDs 214 are activated to stimulate production of the Cannabinoids within the plant. By exposing the Cannabis plant to the emitted light from the LEDs 214, the Cannabinoid concentration within the plant can be increased. By producing a higher concentration of Cannabinoids, the efficiency of the growing operation is increased.

Typically in Cannabis plants, the highest concentration of Cannabinoids is found in the resin which is mostly expressed at the buds of the plant. Since the buds of the plant have the highest concentration of the desired Cannabinoids, it is these that are typically processed to create the Cannabinoid rich extract. The stems, leaves and other portions of the plant have Cannabinoids in lower concentrations that typically make it economically unviable to perform an extraction procedure on the reduced concentration material. However, stimulation of the plant using the LEDs 214 stimulates and promotes the production of Cannabinoids throughout the plant. The higher concentration of the Cannabinoids found in plants grown using the grow light 200, shown in FIG. 2, make processing the lower quality plant material economically viable. Plant material that was typically discarded or sold as a lower quality product can now be refined to produce the high value Cannabinoid rich extract. The ability to process this additional material for extraction again increases the efficiency of the overall process by which the extract is refined or manufactured.

Use of the grow light 200 stimulates Cannabinoid production and concentration throughout the entire Cannabis plant. The increased Cannabinoid levels can allow for whole plant extraction processing. Previously the Cannabinoid concentration was confined to specific parts of the Cannabis plant like the buds and new growth, so these were the parts that were harvested for extraction processing. This additional labor step of separating the plant into harvestable material was a system efficiency compromise between the harvesting and extraction process. The optimized grow light 200 increases Cannabinoid production and concentration throughout the Cannabis plant, allowing the whole Cannabis plant to undergo extraction process rather than just specific portions.

Figure 4C:
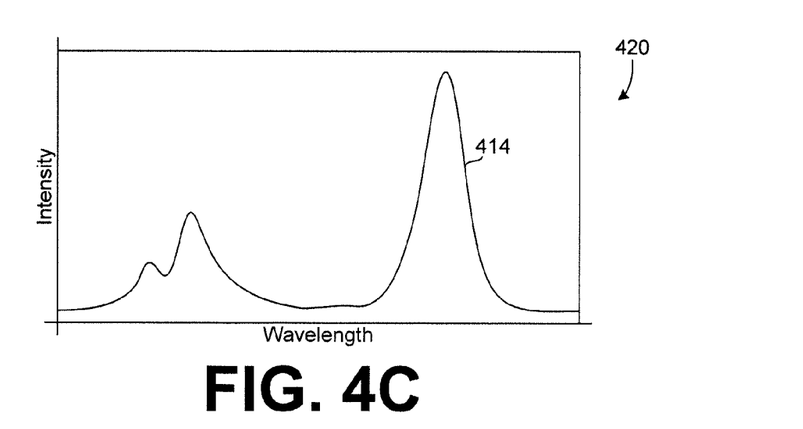
FIG. 4C is an example spectral plot of the first LEDs shown in FIG. 4A and the second LEDs shown in FIG. 4B.

FIG. 4C is an example spectral plot for the light emitted from the grow light 200, showing the combined output of the LEDs 212 and 214.

The LEDs 212 and 214 can be arranged across the face of the substrate 210 to optimize growth of a selected plant(s). The pattern can be based on optimizing the light intensity over a certain area or directing or orienting the emitted light for optimal stimulation or promotion of plant growth. Example embodiments of LED arrangements are shown in FIGS. 3A-3F.

Figure 3A:
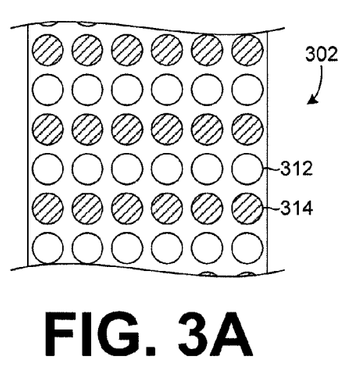
FIGS. 3A-3F illustrate multiple example arrangements of LEDs of the grow light.

FIG. 3A is an example embodiment of an LED arrangement 302 in which the LEDs 212 and 214 are arranged in rows.

Figure 3B:
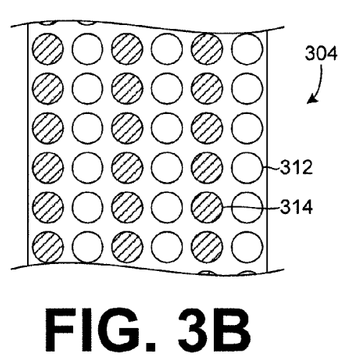

FIG. 3B is an example embodiment of an LED arrangement 304 in which the LEDs 212 and 214 are arranged in columns.

Figure 3C:
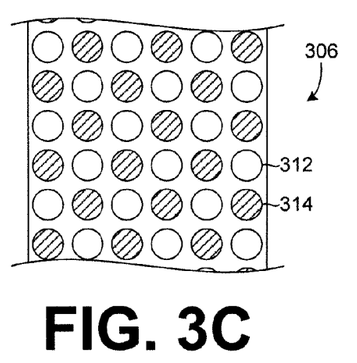

FIG. 3C is an example embodiment of an LED arrangement 306 in which the LEDs 212 and 214 are arranged alternatingly.

Figure 3D:
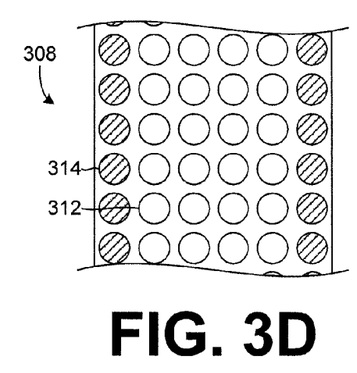

FIG. 3D is an example embodiment of an LED arrangement 408 in which the LEDs 214 run along the long edge of the grow light in single columns and the LEDs 212 fill a center portion of the grow light 200.

Figure 3E:
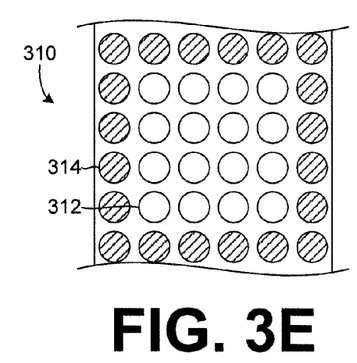

FIG. 3E is an example embodiment of an LED arrangement 310 in which the LEDs 214 form a box about the periphery of the grow light 200 with the LEDs 212 filling a center portion.

Figure 3F:
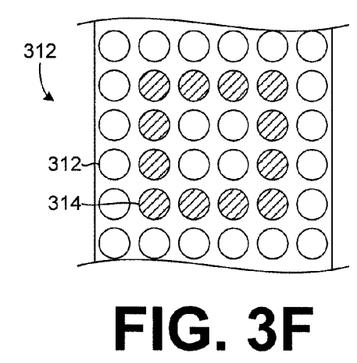

FIG. 3F is an example embodiment of an LED arrangement 312 in which the LEDs 214 form an inner box arrangement with the LEDs 212 arranged about and in the center of the LEDs 114.

The above examples are illustrative of some of the various LEDs, 212 and 214, arrangements possible. Other arrangements can be used to achieve the desired emitted light pattern and intensity levels. Alternatively, additional LEDs emitting additional wavelengths can be added to the arrangement of the LEDs within the grow light to achieve the spectral emission desired.

The selection of the LEDs, based on the emitted wavelength, the phosphor coating and the arrangement of the LEDs can be chosen based on the absorption spectrum of the selected plant. The LEDs 212 and 214 can be selected to stimulate different phases of the selected plant's growing cycle. In the embodiment shown, the first LEDs 112 stimulate a first growth phase and the second LEDs 214 stimulates the second growth phase. Additional LEDs can be added to the grow light 200 to stimulate growth in additional plant phases.

The use of LEDs, such as 212 and 214, that have been selected and optimized for a specific plant allows for increased plant production. By stimulating the photosynthetic activity of the plant, the plant grows and matures faster. This allows the turnover cycle to be increased. Before with non-optimized emitted light, a user may only get two crops in a given time, however, with the optimized light the user may achieve a greater growth capacity, harvesting three or more crops in the same time period. The accelerated growing cycle increases the efficiency and economic returns of the overall system.

Botantical Extraction Method

Figure 5:
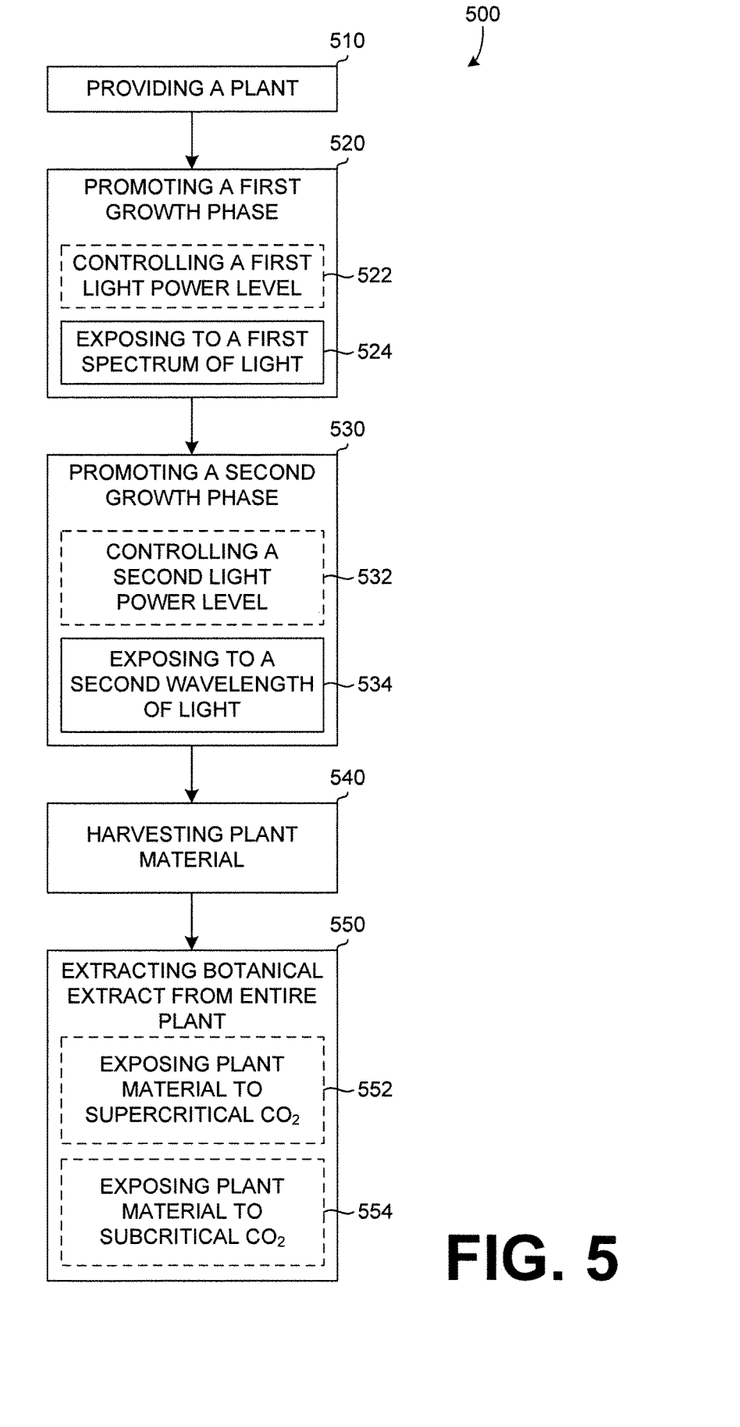
FIG. 5 is a process diagram illustrating the process used to obtain the botanical extract from a plant.

FIG. 5 illustrates a botanical extraction method 500. The plant is selected 510, grown 520 and 530, harvested 540 and then undergoes processing 550 to extract the botanical extract. An initial operation promotes a first stage of growth 520 of the selected plant. A further step promotes a second stage of growth 530 of the selected plant. Once the plant has matured or reached a selected stage of growth, the selected plant undergoes a harvesting operation 540. The harvested plant material then undergoes an extraction operation 550 during which the final botanical extract is refined or manufactured from the material of the selected plant.

In the first operation of the method 500, a plant 510 is selected or chosen. The selection of the plant is based on the desired final botanical extract to be refined or extracted from the plant. The selected plant ideally produces a high concentration of the desired extractable compound(s) or elements.

In an example embodiment, the selection of a plant 510 is from the Cannabis species. The final product, a Cannabinoid rich extract, necessitates the selection of a plant capable of producing and/or storing a high level of Cannabinoids. The method 500 promotes or stimulates the growth of the selected Cannabis plant and further promotes the production of Cannabinoids by the plant. The increased Cannabinoid production by the plant allows for a higher concentration and/or amount of Cannabinoid rich extract can be produced per plant.

An operation 520 promotes a first growth phase of the plant selected in operation 510. In promoting a first growth phase 520, the plant is exposed to a first spectrum of light 524. The first spectrum of light is optimized to stimulate or promote the first growth phase 520 of the plant.

As discussed previously, each plant has a specific absorption spectrum. That is, there is a spectrum of light that is most efficiently used by the plant for its internal processes. The first spectrum of light to which the plant is exposed is optimized to the absorption spectrum of the plant during a first growing phase. In an example embodiment, the first spectrum of light can be emitted from first LEDs that have a first coating and that emit a first wavelength of light. The first wavelength of light and the first coating are selected based on a first absorption spectrum of the plant during a first growth phase. The first wavelength of light emitted by the first LEDs, in conjunction with the first coating, form a first spectrum of light. The first spectrum of light promotes the first growth phase of the plant. Additionally, the first spectrum of light can be achieved using more than a single LED type as necessary to achieve the first spectrum output.

Controlling the first light power level 522, controls the intensity and energy usage of the light used to create the first spectrum. By controlling the first light power level, the first spectrum can be further optimized. Additionally, the energy usage can be monitored, regulated and optimized to increase the efficiency of the method 500.

In an example embodiment, the first growth phase of the Cannabis plant is promoted or stimulated by exposure to a first spectrum of light. The first spectrum of light is optimized to promote the first phase of growth. In the example embodiment, the first phase of growth can be to create a large, leafy Cannabis plant. The large plant and leaf area assist the Cannabis plant in the production of high levels or concentrations of Cannabinoids. The first spectrum of light is emitted by phosphor coated first LEDs. Both the first LEDs and the phosphor coating are selected based on the first absorption spectrum of the Cannabis plant. The selected first LEDs and phosphor coating optimized to stimulate the first growth phase of the Cannabis plant.

An operation 530 stimulates or promotes a second growth phase of the plant selected in operation 510. In promoting a second growth phase 530, the plant is exposed to a second spectrum of light 534. The second spectrum of light is optimized to stimulate or promote the second growth phase 530 of the plant.

The second spectrum of light is optimized to a second absorption spectrum of the plant during a second growth phase. A second growth phase can be a continuation of the growing of the plant or can be a secondary plant life stage such as flowering or fruiting. Stimulation of the plant during the second growth phase promotes the biological processes within the plant during the second growth phase. As with the operation 520, the second spectrum of light can be emitted by second LEDs that emit a second wavelength of light. The second wavelength and second LEDs can be the same as or different from the first LEDs and first wavelength. The second LEDs emit a second spectrum of light. The second spectrum of light can be altered with the inclusion of a second coating on the second LEDs. The second coating would alter the light emitted from the second LEDs. The emitted light from the second LEDs is optimized to promote the second growth phase of the plant. Additionally, the second spectrum of light can be achieved using more than a single LED type as necessary to achieve the second spectrum output.

Controlling the second light power level 532, controls the intensity and energy usage of the light used create the second spectrum. By controlling the second light power level, the second spectrum can be further optimized. Additionally, the energy usage can be monitored, regulated and optimized to increase the efficiency of the method 500.

In an example embodiment, the second growth phase of the Cannabis plant is promoted or stimulated by exposure to a second spectrum of light. The second spectrum of light is optimized to promote the second phase of growth. In the example embodiment, the second phase of growth can be to create buds and increase production of Cannabinoids. During this second phase, the desired extractable compounds, the Cannabinoids, are produced and concentrated throughout the plant. Promotion of the second growth phase increase the Cannabinoid content in parts of the plant that would normally not be used during traditional extraction procedures. The increased Cannabinoid concentration in these parts allows them to be used in the extraction process which further increases the efficiency and economic returns of the method 500.

Once the plant has reached a desired or required phase of growth, it can undergo a harvesting operation 540. The harvesting operation 540 collects and prepares the plant material to undergo an extraction process.

In an example embodiment, the Cannabis plant has matured with an optimized amount of Cannabinoid production and storage having occurred. When the Cannabis plant is at this stage it may be harvested and collected. During this operation the Cannabinoid containing parts of the plant are collected and prepared for the extraction operation. As discussed above, the whole plant can be collected and prepared for the extraction process. The harvesting operation 540 can include collecting the Cannabinoid resin laden buds of the Cannabis plant and collecting and preparing the Cannabis stems and leaves.

An extracting operation 550 is performed on the plant material harvested in operation 540. During the extraction operation 550, the plant undergoes processing to remove compounds from the plant material. The extraction operation can target specific desired compounds or can be an untargeted operation that creates an extract rich product. The extract rich product can then be further refined to concentrate the desired compounds. Examples of possible extraction processes include extraction using a solvent or heat.

In an example embodiment, the Cannabis plant material undergoes a supercritical 552 or subcritical $CO_2$ 554 extraction process. The supercritical 552 or subcritical $CO_2$ 554 is permeated through the Cannabis plant material, extracting the Cannabinoids. The Cannabinoids are then isolated or refined from the supercritical 552 or subcritical $CO_2$ 554 solvent. The final product, a Cannabinoid rich extract, can then be used in a multitude of recreational and pharmacological processes.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A light source for a grow light, comprising:
a housing;
a plurality of first light emitting diodes (LEDs) having a first coating and a first maximum operating power, the plurality of first LEDs configured to emit a first wavelength of light towards a cannabis plant and further configured to be controlled by a first switch;
a plurality of second LEDs having a second maximum operating power and configured to emit a second wavelength of light towards the cannabis plant and further configured to be controlled by a second switch separately controllable from the first switch;
wherein the plurality of first LEDs and the plurality of second LEDs are both positioned in the housing and are arranged in a configuration that defines a perimeter and a center portion, the plurality of first LEDs arranged along at least a portion of the perimeter and the plurality of second LEDs arranged in the center portion,
wherein the first LEDs, the first coating and the second LEDs are selected based on an absorption spectra of the cannabis plant, and
wherein the plurality of first LEDs are configured to be operated at a power value less than the first maximum operating power of the plurality of first LEDs and the plurality of second LEDs are operated at a power value less than the second maximum operating power of the plurality of second LEDs.

2. The light source for a grow light of claim 1, wherein the first coating of the first LEDs includes phosphor.

3. The light source for a grow light of claim 2, wherein the first coating is structured to diffuse the emitted first wavelength into a first spectrum.

4. The light source for a grow light of claim 3, wherein the first spectrum corresponds to an absorption spectrum of the cannabis plant during a portion of a growth phase of the cannabis plant.

5. The light source for a grow light of claim 1, wherein the second LEDs have a second coating.

6. The light source for a grow light of claim 5, wherein the second coating of the second LEDs includes phosphor.

7. The light source for a grow light of claim 6, wherein the second coating is structured to diffuse the emitted second wavelength into a second spectrum.

8. The light source for a grow light of claim 7, wherein the second spectrum corresponds to an absorption spectrum of the plant during a portion of a growth phase of the cannabis plant.

9. The light source for a grow light of claim 1, wherein the cannabis plant has a plurality of distinct growth phases, each of the plurality of growth phases having a corresponding absorption spectrum; and,
the plurality of first LEDs, the plurality of second LEDs, and the first coating are selected based on the absorption spectrum of each of the plurality of growth phases.

10. The light source for a grow light of claim 1, wherein the plurality of first LEDs and the plurality of second LEDs are arranged in at least one of alternating horizontal rows, alternating vertical rows and alternating diagonals.

11. The light source for a grow light of claim 1, wherein the power value less than the first maximum operating power is approximately 63% of the first maximum operating power.

12. The light source for a grow light of claim 1, wherein the plurality of first LEDs generate a first level of heat during operation and the plurality of second LEDs generate a second level of heat during operation, and wherein a combined temperature output of the first level of heat and the second level of heat is 120° F. or less.

13. A system for refining a botanical extract, comprising:
an LED grow light having a plurality of first LEDs having a first coating and configured to emit a first wavelength of light towards a cannabis plant and a plurality of second LEDs configured to emit a second wavelength of light towards the cannabis plant, the plurality of first LEDs and the plurality of second LEDs both positioned in a housing and arranged in a configuration that defines a perimeter and a center portion, the plurality of first LEDs arranged along at least a portion of the perimeter and the plurality of second LEDs arranged in the center portion;
wherein the cannabis plant has a plurality of growth phases, each of the plurality of growth phases having a corresponding absorption spectrum, and
wherein the plurality of first LEDs are selected based on an absorption spectrum of a first growth phase and the plurality of second LEDs are selected based on an absorption spectrum of a second growth phase, and
wherein the plurality of first LEDs are configured to be controlled by a first switch and the plurality of second LEDs are configured to be controlled by a second switch that is separate from the first switch, and
wherein the plurality of first LEDs are operated at a power value less than a first maximum operating power of the plurality of first LEDs and the plurality of second LEDs are configured to be operated at a power value less than a second maximum operating power of the plurality of second LEDs; and
a supercritical carbon dioxide extractor configured to receive the cannabis plant after the first growth phase and the second growth phase are complete and further configured to extract at least a botanical extract from the cannabis plant.

14. The system for refining a botanical extract of claim 13, wherein the first coating of the plurality of first LEDs includes phosphor.

15. The system for refining a botanical extract of claim 14, wherein the first coating is structured to diffuse the emitted first wavelength into a first spectrum that corresponds to the absorption spectrum of the first growth phase.

16. The system for refining a botanical extract of claim 13, wherein the plurality of second LEDs have a second coating.

17. The system for refining a botanical extract of claim 16, wherein the second coating includes at least one of phosphor and a polymer.

18. The system for refining a botanical extract of claim 13, wherein the power value less than the first maximum operating power is approximately 63% of the first maximum operating power.

19. A botanical extraction method, comprising:
providing a cannabis plant;
promoting the cannabis plant to grow in a first growth phase and a second growth phase of a growth cycle of the cannabis plant by:
exposing the cannabis plant to a first wavelength of light emitted from a plurality of first LEDs coated with a first coating, the first wavelength of light and the first coating selected based on an absorption spectrum of the plant during the first growth phase, the plurality of first LEDs having a first maximum operating power, the exposing the cannabis plant to the first wavelength of light emitted from the plurality of first LEDs includes operating the first plurality of LEDs at a power value less than the first maximum operating power;
exposing the cannabis plant to a second wavelength of light emitted from a plurality of second LEDs, the second wavelength of light selected based on an absorption spectrum of the plant during the second growth phase, the plurality of second LEDs having a second maximum operating power, the exposing the cannabis plant to the second wavelength of light emitted from the plurality of second LEDs includes operating the second plurality of LEDs at a power value less than the second maximum operating power, wherein the plurality of first LEDs and the plurality of second LEDs both positioned in a housing and arranged in a configuration that defines a perimeter and a center portion, the plurality of first LEDs arranged along at least a portion of the perimeter and the plurality of second LEDs arranged in the center portion;
harvesting the cannabis plant in its entirety when the first growth phase and the second growth phase are complete; and,
extracting a botanical extract from the entire harvested cannabis plant using a supercritical carbon dioxide extraction process.

20. The method of manufacturing a botanical extract of claim 18, further comprising: controlling the plurality of first LEDs using a first switch, and
separately controlling the plurality of second LEDs using a second switch.

21. The method of manufacturing a botanical extract of claim 18, wherein the entire harvested cannabis plant includes at least the leaves and the trim of the cannabis plant.

* * * * *